United States Patent [19]

Brownlee

[11] 4,313,828
[45] Feb. 2, 1982

[54] HIGH PRESSURE TUBING COUPLER

[75] Inventor: Robert Brownlee, Santa Clara, Calif.

[73] Assignee: Brownlee Labs, Inc., Santa Clara, Calif.

[21] Appl. No.: 23,954

[22] Filed: Mar. 26, 1979

[51] Int. Cl.³ .............................................. B01D 15/08
[52] U.S. Cl. ................................. 210/198.2; 55/386; 285/109
[58] Field of Search ...................... 210/198 C; 55/386; 285/10, 13, 70, 80, 107–109

[56] References Cited

U.S. PATENT DOCUMENTS

| | | | |
|---|---|---|---|
| 3,679,237 | 7/1972 | De Angelis | 285/109 |
| 4,002,186 | 1/1977 | Fink et al. | 285/80 |
| 4,026,803 | 5/1977 | Abrahams et al. | 210/198 C |
| 4,083,702 | 4/1978 | Hartigan | 210/198 C |

Primary Examiner—John Adee
Attorney, Agent, or Firm—Robert B. Block

[57] ABSTRACT

A coupler or union for passing fluid under pressure from a column or tube in which the tube is received within a chamber in fluid communication through the floor within said coupler and forming a zero dead volume seal therewith, an annular recess in the coupler or union surrounding the tube or column and containing a balanced hydraulic seal in contact with the recess wall and tube or column and opening in communication toward said dead volume seal so that leakage from the latter under high pressure fills and activates the balanced hydraulic seal to the line pressure. The coupler or union is particularly applicable for high pressure liquid chromatograph column connections.

10 Claims, 4 Drawing Figures

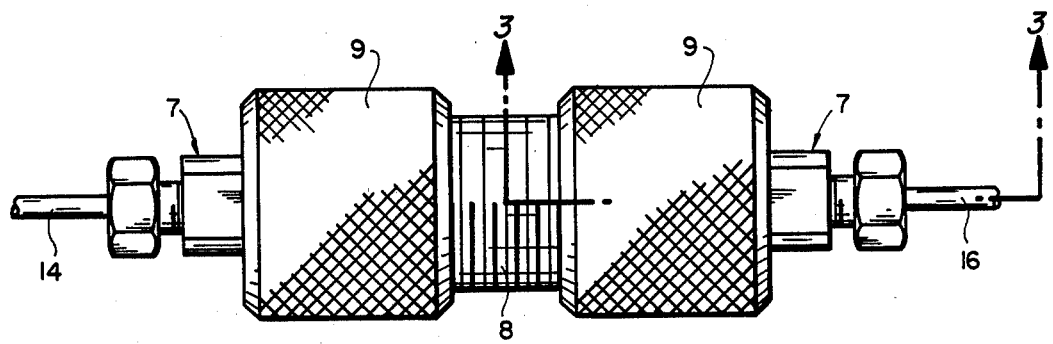
FIG._1
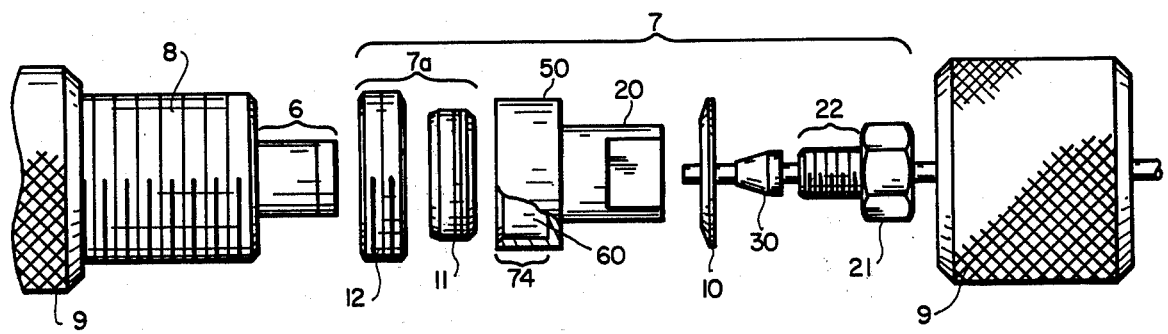
FIG._2
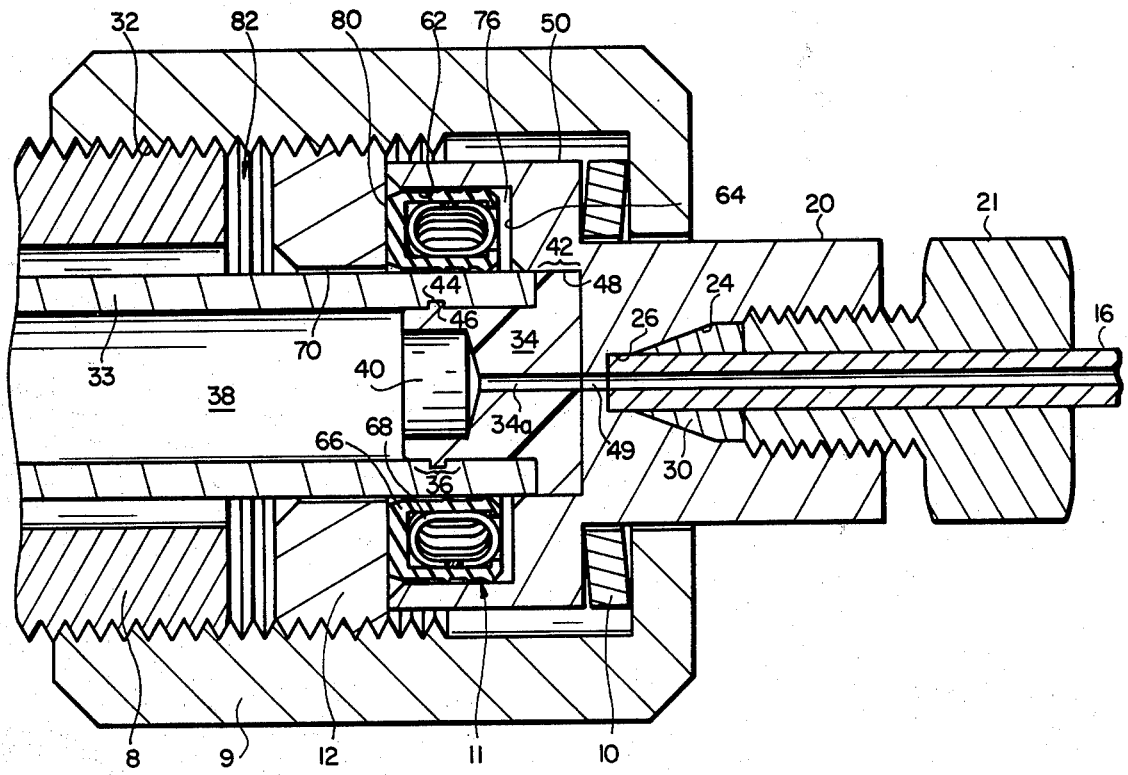
FIG._3

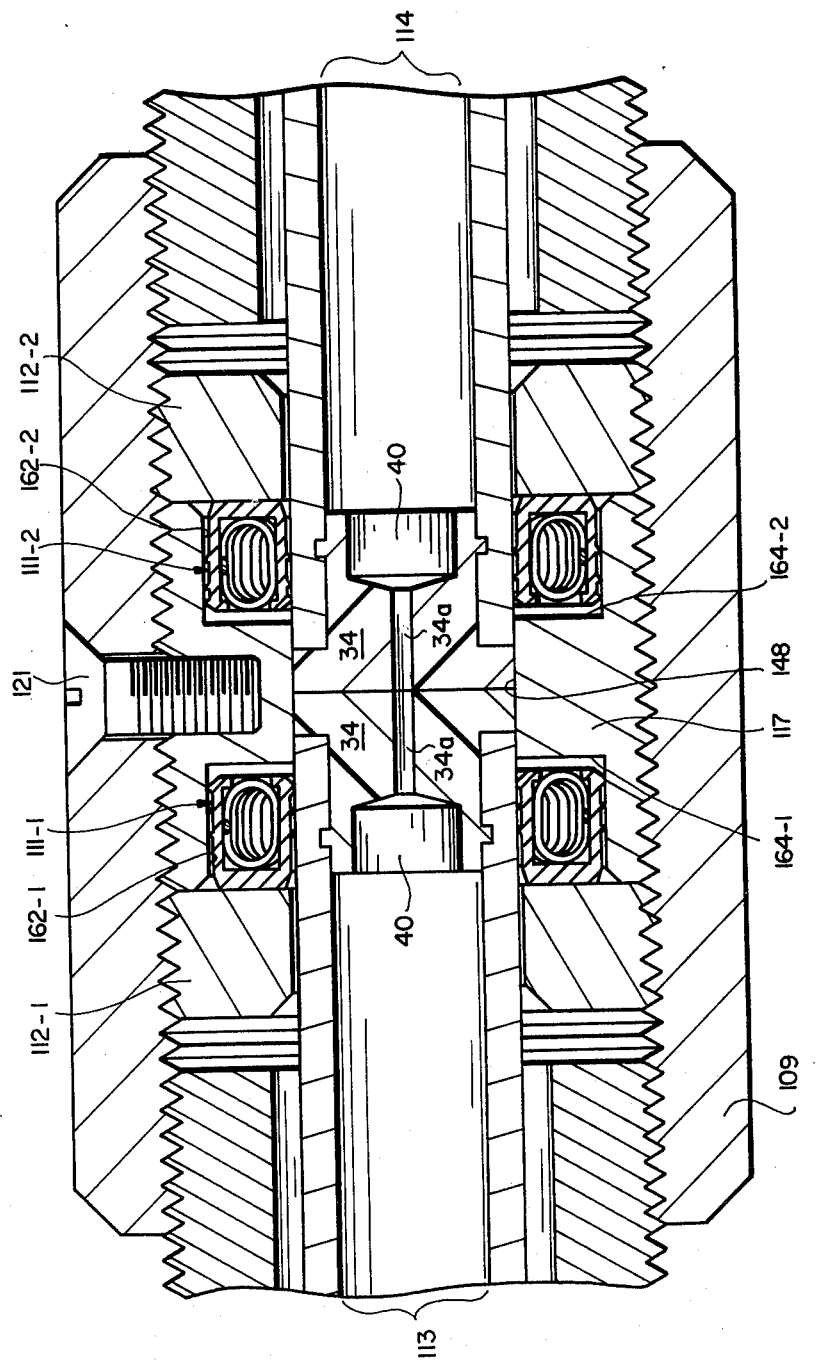

HIGH PRESSURE TUBING COUPLER

CROSS REFERENCE TO RELATED APPLICATION

Reference is made to co-pending application of the present inventor entitled CARTRIDGE TYPE SEPARATION COLUMN AND HOLDER ASSEMBLY FOR LIQUID CHROMATOGRAPHS filed Aug. 24, 1978, Ser. No. 936,400, abandoned subsequently continued as Ser. No. 116,468 and now issued as U.S. Pat. No. 4,283,280 on Aug. 11, 1981.

TECHNICAL FIELD OF THE INVENTION

This invention relates to high pressure liquid chromatography column and tube couplers wherein it is desired to connect an elution column to an associated liquid chromatograph pumping system solely by hand tightening of coupler elements without tools.

More generally the invention can be applied as a coupler or union in any high pressure system and therefore is a general purpose device providing a low dead volume, high pressure seal between the connected parts.

DEFINITIONS

As used herein the abbreviation HPLC shall mean high prssure liquid chromatograph(y) and may be used interchangeably therewith. HPLC indicates operation of an LC elution column at pressures substantially higher than 500 psi. Generally HPLC pressures are in the range of 3,000 psi to 8,000 psi. LC shall mean liquid chromatograph(y) and may be used interchangeably therewith. Tube or tubing shall include pipe and piping and may be used interchangeably with each other and with the latter. An LC elution column includes a system of tubing and is included within the foregoing definition of tube or tubing. As used herein the word coupler is meant in its generic sense and shall include union, or any form of distribution system having a port or pipe from or to which liquid under high pressure is being delivered or received. If intended to be more specific, such other expressions as union and the like will be used. Zero dead volume means that fluid passing through channel; bore, or passageway is confined to flowing motion and has no way to enter into a space in which no flow occurs from which it could gradually re-enter the column and adversely affect the separation process which depends on differential migration of components in a mobile phase passing through the column and capable of being cleared completely between samples. As used herein, the zero dead volume does not preclude leakage from the means for achieving the same.

BACKGROUND AND PRIOR ART

Heretofore, one common method of sealing an end fitting into engagement with an HPLC elution column has required the use of tools such as wrenches to make up the sealing arrangement, usually with a compression fitting. Such compression fittings are quite reliable for high pressure liquid chromatography and rely on a radially driven metal to metal seal using a cone shaped ferrule driven into a cone shaped recess which squeezes it into radial compression against the HPLC column. While quite reliable when properly made up, they do require the use of tools and can be over tightened or insufficiently tightened depending upon the skill of the operator. It is very difficult to assess whether or not this type of seal has been made up properly, particularly for high pressure operations, i.e. at 5,000 psi or above. Another type of column and end fitting seal for HPLC uses relies on a metal to metal gasket interposed between the end fitting and the column sealing faces. While this provides a reliable seal, it is not capable of being reused if dismantled. For use at lower pressures, reference is made to the cross-referenced U.S. Pat. No. 4,283,280 which is incorporated herein by reference. In that application a hand-tightenable sealing arrangement is disclosed in which a poly tetrafuoroethylene (PTFE) or other plastic end piece forms a gasket laterally extending over each end of the column tube. This piece is subject to cold flow and therefore the design in said application calls for an arrangement in which the PTFE end piece sealing portion is completely contained within a chamber formed in the end fitting into which the column is inserted. This chamber provides a floor and side walls in such close fitting relation to the end piece that cold flow is effectively prevented. The cross-referenced application discloses that a Belville washer interposed between the end fitting and a drive nut permits hand tightening of the drive nut to compress the Belville washer which in turn transmits through a small deflection the required sealing force for medium pressure work. More specifically, that design has been found to work reliably up to 500 psi and is sufficient for many applications. However, it has been found that this design cannot be taken to HPLC pressures (i.e. 5,000 psi and higher) with sufficient reliability. There is, therefore, a need for a column coupler for use in high pressure liquid chromatographic applications.

There is particularly a need for a high pressure liquid chromatographic coupler which has few parts and which can be made up many times to a reliable sealing engagement without any free parts in the arrangement and by a hand tightening operation.

OBJECTS OF THE INVENTION

It is the general object of the present invention to provide a new and improved HPLC seal and coupler assembly for liquid chromatographs which will overcome the above limitations and disadvantages. A further object of the invention is to provide a coupler of the above character which can be hand tightened to HPLC design specifications and which is reliable upon repeated disassembly and remaking.

Another object of the invention is to provide a column coupler for use in HPLC operations in which the column is removeable from the coupler by hand untightening operation and replaceable HPLC with a hand tightening operation to a reliable sealing strength and which has few, if any parts during such replacements.

It is a further object of the invention to provide a coupler of the above character which is reuseable for HPLC work.

A more general object of the present invention is to provide a coupler or union for use in any high pressure liquid or fluid movement system by which a tubing can be readily, easily and reliably connected and disconnected from a part of the system into which it is desired to establish communication.

It is a further object of the invention to provide a guard column construction by which HPLC liquid chromotograph systems employing an expensive analytical column can be protected from impurities which shorten the potential lifetime of the analytical column and which guard column does not degrade the performance of the system.

SUMMARY OF THE INVENTION

For use in HPLC, the present invention employs a replaceable cartridge type separation column and seal which consists of an elongate hollow metal tube having an end seal assembly provided with a laterally extending portion forming a seal integrally formed with the plug, the seal overlaps the end of each end of the volume tube to present a transverse extending flat annular seal covering at each end. A pair of end fittings having a precisely matching recess form a chamber therein overlap each end of the column and seal for receiving the same. Knurled cap (compression) nuts adapted for being hand-tightened engage each end of an elongate holder barrel (of slightly less length than the column cartridge assembly) and through which the column is disposed, the cap nuts bearing upon the end fittings through spring washers of the Belville type. The cap nuts engage open threads at each end of the barrel so that tightening of the nuts is sufficient to put the holder in tension and to load the spring washers to create a compression seal of the plastic between the ends of the tube and the means forming the bottom of the recess in the end fittings. The load applied by deformation of the spring washers, is adequate to obtain a compression seal on the plastic seals which are totally confined laterally by the close-fitting dimensioning of the chamber in each end fitting.

The present invention is predicated upon the realization that an additional modification and the second sealing feature can be combined with the sealing mechanism of the above description to provide a reliable hand tightenable HPLC seal. More specifically, the end fitting is further provided with an annular recess spaced from the chamber and in fluid communication therewith. The annular recess provides an annular opening into which a plastic balanced hydraulic seal of annular form is positioned, the balanced seal being dimensioned to lie in close fitting contact between the column and the wall radially defining the annular recess in the end fitting. A retaining ring, carried by the compression cap nut holds the balanced seal in position during assembly and disassembly and until loaded. The balanced hydraulic seal is U-shaped in radial cross-sectioned and opens towards the aforementioned chamber and first seal. Since the first seal is assumed to leak eventually at high pressures, it leaks into and fills the balanced hydraulic seal to the pressure passing between the tube and end fitting (coupler) causing radial forces to be applied of equal magnitude between the column tube and the wall of the annular recess to thereby effect automatic sealing to the same high pressure as is being passed through the coupler or end fitting.

This type of high pressure seal should find application not only in high pressure liquid chromatography but also in other high pressure fluid piping systems having low or zero dead volume requirements. In the present disclosure, emphasis will be given to a construction whereby an exceptionally efficient guard volume is constructed for employment as a protective measure, in series, at the input of the principle analytical column of high pressure liquid chromatographs. A further example will be given, wherein virtually all plumbing between such guard column and the main elution to column (of a HPLC system) is eliminated by a union coupler. Incorporating a unitary pair of couplers constructed in accordance with the present invention in which the end seal (of each one of a pair of the guard and analytical columns) serves as the means for defining the bottom of the chamber for the other, the columns being placed, in compression, into direct end-to-end contact.

It is another object of the present invention to provide a unique, easily replaceable, guard or column and mounting union, in which the analytical column and guard column are in end-to-end direct coupling contact and sealed together, to form with the associated fitting zero volume first seal, thereby eliminating all intervening connections usually required in employing a guard column type arrangement.

It is another object of the present invention to provide a general purpose tubing coupler, which has wide usefulness for applications requiring zero dead volume transfer of liquids under pressure.

These and other objects and features of the invention will become apparent from the following description with taken in conjunction with the accompanying claims and the appended drawings of which:

BRIEF DESCRIPTION OF THE DRAWINGS

FIG. 1 is a plan view of the high pressure liquid chromatograph column coupler as constructed in accordance with the present invention for use at high pressures.

FIG. 2 is a plan view of the coupler of FIG. 1 showing one end thereof in exploded view, the other end thereof (not shown) being identical in construction.

FIG. 3 is a cross-sectional view of one end of the coupler of FIG. 1 taken along the lines 3—3 thereof.

FIG. 4 is a cross sectional view of a union designed for direct column-to-column coupling between an analytical HPLC column and a guard column and constructed in accordance with the present invention.

DETAILED DESCRIPTION OF THE PREFERRED EMBODIMENTS

Referring in general to FIGS. 1 and 2, the present invention includes an LC column 6 together with end plugs closing each end to form a self contained replaceable cartridge; an end fitting assembly 7 including a fluid seal ring assembly 7a; a cartridge barrel or holder 8 and retaining cap nuts 9 for bearing on Bellville spring washers 10 interposed between them and the respective end fitting for interconnecting the parts into a well sealed and operative relationship to each other. The end fitting contains and supports as a unitary assembly the sealing and coupling system including the ball seal 11 and retaining ring 12. The HPLC column and holder assembly is symetrical, its inlet and outlet parts being identical and interchangeable and therefore reversible. Accordingly, the description herein will be given in the singular with reference to one end of the assembly but should be understood to include both, in connection with the embodiment of FIGS. 1–3.

Referring particularly to the exploded portions of FIG. 2 and to the detailed assembly drawing of FIG. 3, the inlet tubing 14 (from the HPLC pump injection system, not shown) and outlet tubing 16 (to the remainder of the liquid chromatograph and detector) pass freely through end cap nut 9 and spring washer 10 into a capillary engaging portion of the respective end fitting 17 which includes an outwardly facing internally threaded projection 20 engagedly an externally threaded compression drive nut 21. These serve as part of means provided at each end of the column and holder assembly of the present invention for sealably engaging a semiflexible tubing which interconnects the assembly to an associated liquid chromatograph. Since this connection will not need to be unmade, it is preferably the type which may remain relatively permanently installed. A variety of such connections are known, an example of which is illustrated in the drawings and is available under the trademark "Swagelok" as manufactured by Crawford Fitting Company of Cleveland, Ohio. Its remaining elements include a threaded section 22 followed by a conical section 24 tapering down to a capillary receiving recess 26, the latter being dimensioned to establish a close fitting relation with the end of the capillary. The tapered section is adapted to receive and cooperate with a conical compression ferrule 30. When tightened to specification the compression nut 21 provides a high pressure seal by radial compression of the ferrule 30 against the tubing 14, 16.

The inward column facing end of each cap nut 9 has a recess opening 32 which is internally threaded and adapted to engage the cartridge barrell 8. The other end of the end cap is closed except for a central passage through which a capillary and capillary receiving projection 20 of an end fitting is permitted to freely pass. These parts are shown assembled in FIG. 3.

Referring now particularly to FIG. 3, the column includes an elongate cylindrical tube 33 closed at each end with an end plug 34 as shown in detail in cross-section and having an entry port 34a for admitting liquid flow therethrough. The end plug is designed to serve three functions. The first is as a plug by providing a portion 35 to terminate the end of the column and to retain packing 38 therein and the second is a carrier for an internally mounted filter unit 40. Thirdly, it provides a laterally extending portion 42 which overlaps the end of the column tube to form a gasket or seal which is the same diameter as the tube. The plug portion is about the same diameter as the inner diameter of the tube and extends internally therein in close fitting relation. Preferably, it is provided with a radially extending circumferential projection or rim 44 which interfits within a mating groove 46 machined at a depth to permit engagement by the projection when the plug is fully inserted. In this way the end plug is biased to remain in position during apparatus disassembly notwithstanding the close fitting relationship between the seal plug and the end fitting since the captured projection in the groove of the tube requires more force to unmake than the close sliding fit created between the seal and the end fitting 7. The filter can be of any suitable type such as a fine screen or sintered stainless steel frit and slidably inserted within a recess on the inner side of the plug. While the filter can be independently replaceable, it is usually more convenient to maintain a supply of seal plugs with filters installed so that the latter becomes a disposable and replaceable sub-assembly.

As shown, the end fitting is provided at its inner extreme with a recess 48 which is the same dimension as the column tube and seal portion 42 of the plug and provides a chamber for receiving the end of the cartridge and seal. A bore 49 is the fitting communicates between the port through the column end plug and the capillary tubing 16. The assembled cartridge is captured within the chamber end fitting in a very close fitting relationship, contact being established between the outer, or endwise facing flat of the seal plug and the chamber floor 48a as well as between the seal and the side wall of the recess 48. In this way the laterally extending seal portions of the seal plug form a gasket like structure totally bounded at the outer extreme by the lower and/or floor of the chamber and at its lateral sides by the side walls thereof. The plug can be made of any suitable inert plastic, but is preferably made out of polytetrafluoroethylene (PTFE). However, since PTFE is only machinable, it may be desired to make the plug out of other similar materials which can be molded or extruded, such as polyfluoropropylene (FEP). The Bellville compression spring 10 is interposed between a laterally enlarged portion 50 of the end fitting surrounding the seal plug and tube receiving recess therein, so that when assembled, the compression spring is engaged between the end cap and cartridge ends to establish the magnitude of the sealing force of engagement between the end fitting and the seal of the cartridge assembly.

The end cap has certain physical dimensions which have been found to be particularly appropriate for use in the present application. Specifically, it is cut from $\frac{3}{4}$ diameter stock so that its nominal outer dimension is that size. The minimum outer dimension that would be suitable for handtightening operation is believed to be about $\frac{1}{2}$ inch or greater and the range is preferably of the order of $\frac{5}{8}$ to an inch. The inner threads of the end cap are 9/16 inch in diameter with 18 threads per inch as are the outer threads of the elongate tube holder. The spring washer compression force for flattening is approximately 130 pounds within about 0.009 inch travel. It can be readily shown that this combination or approximately this combination produces an assembly which may be hand-tightened to its designed specification by a person of relatively low strength and at the same time cannot be overtightened by a person of above average strength. Accordingly, the seal procuded thereby is capable of achieving the design sealing specification without danger of being mishandled by operating personnel using the Bellville washer which required displacement of 9/1000 of an inch to achieve design compression of 130 pounds. This portion of the assembled unit was found to reliably achieve a reproducable seal of 500 psi which is adequate as a first sealing element in the present invention. While tests showed that the seal achieved sealing forces of the order of 5,000 psi for a limited time, these cannot be reliably achieved with this seal alone.

The following additional specification compliment the description as given above. The column tube is constructed of 316 stainless steel LiChroma ID, $\frac{1}{4}$ inch in diameter, internal diameter of the tube 0.180, external diameter of plug portion of seal plug 0.73, diameter of rim projection on seal plug 0.180, depth of filter element and associated recess 0.060 inches, depth of overlap seal at other end of seal plug 0.050 inches, diameter 0.250 inches. Cartridge assembly recess diameter 0.255 inches, depth 0.06 inches. The holder 8 and cap nuts 9 are aluminum; the end fitting, washer 10, and retaining ring 12 are stainless steel.

As mentioned, the cartridge column, holder and associated parts are identical at each end as are all of the parts so that the device can even be reversably assembled. In addition, the holder is somewhat shorter than the overall length of column including seal plugs so that compression force can be delivered by the end caps without interference which would be caused by engaging the ends of the holder itself.

Referring now again to FIG. 3, means are provided for establishing a balanced, liquid pressure operated or actuated seal between the fitting and the column retained therein. This balanced seal enables the coupler to serve in high pressure liquid chromatographic applications up to pressures as high, for example, as 10,000 psi. Such means includes an annular recess 60 having an outer lateral wall 62 of cylindrical form extending radially in spaced relation with respect to the wall of the tube of the analytical column and having an annular floor portion 64 returning to the column diameter and communicating with the side wall 48 of the first recess or chamber. The flexible balanced liquid pressure seal 11 is disposed in the annular region defined by said second recess and is dimensioned to lie in close fitting contact between the tube 33 of the column and the aforementioned wall 62 defining the annular recess.

The balanced seal comprises a flexible member 66 in the form of a partial torodial shell having one end face removed so that it is U-shaped in radial cross section with an opening 68 facing towards the first recess 42. Means are provided within the balanced seal for yieldably urging the same into intitial sealing contact between the outer wall 62 of the recess and the wall of the contained tube 33 and for providing a low pressure seal of a mechanical nature and to establish the initial structural stability of the parts. Such means consists of an annular spiral spring 68 (referred to as a garter spring) inserted in the interior hollow of the plastic member seal, the coils of which are canted to the radial of the ring to provide radial deflection and to preload the same for inward and outward expansion within the physical limits of the parts. Means are provided for retaining the balanced seal in position within the annular recess and consists of the outwardly threaded seal ring 12 having a central passageway 70 there through for permitting passage of the column into the fitting and outwardly facing threads 72. The retaining ring is threaded in engagement with the threads 32 of the knurled nut and taken into touching contact with the column facing portion of the second end of the fitting where it is retained in position by application of a releasable adhesive such as Lock-tit. It will be noted that the depth of the recess as indicated by the number 74 is greater than the axial dimension of the balanced seal providing a gap of 0.03 inches indicated at 76. This gap or space allows for leakage from the end seal recess to flow along wall 48 and into open side face of the balanced seal and to create therein, when filled, a uniform liquid pressure which is directed equally in all directions and thus forms a seal by expansion of the seal inner and outer walls into contact with the fitting and the column tubing. In this way whatever pressure of liquid is being transferred through the fitting fills the balanced seal to the same pressure and creates a balanced condition in which the sealing forces against the walls laterally retaining the wall balance seal to create a good seal up to the design pressures of the particular balanced seal employed.

The toroidal shell of the balanced seal is preferably made of a chemically inert flexible plastic having good contact sealing properties, polytetrafluoroethylene (available under the trademark Teflon from DuPont), is an excellent sealing material for this application, however, polytetrafluoroethylene impregnated with stiffening material may also be used as may polytetrafluoropropylene.

ASSEMBLY AND DISASSEMBLY

Assembly and disassembly of the device is very simple. Assuming that the device is in the form shown in FIG. 3, final assembly consists of continuing to rotate the nut 9 so as to bring the compression washer 10 flat, as indicated. This involves a movement of a few thousandths of an inch. In this particular case the retaining ring is made of stainless steel as is the fitting and since they are in contact with each other when the fitting is partially disassembled as shown in FIG. 3 they make sliding contact at their interface at 80. As the nut 9 is tightened however and the Bellville washer flattened, a clearance appears at that interface thereby relieving the friction which would otherwise exist. This small clearance does not materially effect function of the retaining ring in keeping the balanced seal in position. At the other end there is a minimal amount of friction between the stainless steel Bellville washer and the aluminum driving material of the surface of the nut 9 since these materials have a lower coefficient of sliding friction than stainless steel against itself. It should be noted that the barrel 8 and the ring are so dimensioned to create a relief gap at 82 to accommodate movement of the ring into proximity but not contact with the barrel.

From an assembled position, the disassembly involves simple finger rotation of the cap nut to unscrew the same from the barrel or column holder. As this takes place the retaining ring ultimately provides the driving force to remove the fitting. However the Bellville washer has been released and very little additional clearance is required to create a freely moving arrangement. It will be noted that when disassembled the retaining ring holds the balanced seal in position and thereby creates together with the cap nut and the end fitting an entirely unitary structure having no free parts. The column itself is also a unitary structure since the end plug retains the same together with the sorbant in a non-dismountable arrangement at least insofar as disassembly of these components is concerned. The free parts available upon disassembly thus are only: (1) the nut 9 and end fitting assembly, (2) the column itself, and (3) the holder or barrel.

While the seal of the present invention is generally useful, particularly in liquid chromatography for both the analytical column mountings and for the guard column mountings, its simplicity and ease of reuse at high pressures lends itself to wide application as a guard column device. It has been found that typical sorbants utilized in liquid chromatography can be employed as sorbant in the guard column and that the latter by compromise can usually serve its purpose within an effective length of about 3 centimeters. Cost considerations indicate that at least half of the cost of maintaining an operative analytical column can be saved by employing and replacing at frequent intervals a guard column to protect the main analytical column. Since its active sorbant is the same as that of the analytical column it not only improves the lifetime of the analytical column and maintains its high performance but does so without sacrifice of performance. The reason for this is that while there may be some degrading feature due to additional piping, tubing and other elements in order to install and insert the guard column it also provides a short additional length in the overall separation system. By choosing a length of 3 centimeters it is found that this additional length is insufficient to adversely effect the separated components of the sample being passed on the one hand and yet on the other hand is adequate to stop impurities from arriving at the analytical column. The guard column removes both physical impurities by reason of the mechanical frit or other filter element 40 located at each of its ends. In addition those chemical components which are retained by the column irreversibly are captured within the length of the guard column. More specifically, there are chemical components which are entirely soluble in the solvent carrier used in liquid chromatography but which are so strongly retained by the material of the sorbant that they are either irreversibly or so strongly retained as to clog the system and eventually necessitate replacement of the expensive analytical column. Such materials include essential oils, fragrent natural products from plants which for example contain aromatic and natural oil products of high molecular weight. Very few injections through a separation column of material containing these components will result in contamination of the analytical column beyond further utility. Also, in the analysis of biogenic amines and other bio-origin liquid soluble samples pose similar problems. Proteins, for example, contained in serum would tend to clog an analytical column. Therefore, the use of a disposable short length guard column is extremely useful. The considerations relating to the length of the column are that it should be as short as possible so that it does not become a significant factor in the analytical separation being performed. However, there is a practical limit. If it is made shorter than a certain amount there is no significant cost advantage and may lack if shorter than 3 centimeters sufficient chemical filtering property to be able to last. Thus the length of 3 centimeters is a compromise and is also a practical length enabling the use of hand tightening knurled nuts and the human factor the size of the hand and use of fingers so as to be employed with ease.

OPERATION OF BALANCED SEAL

In operation, the device works because of the leakage from the first face-to-face seal the primary function of which is to provide a zero dead volume for the end of the column so that the sample does not leak into an available space from which it can migrate back into the system at a later time when loaded to capacity. The contained air or other gases within the liquid within the ball seal naturally migrate out of the system and a quite stable state is established in which there is no further communication between the balanced seal and the passageways through which samples under analysis are being passed in a mobile phase. It should be noted that leakage of the first seal is essential to the operation of the device and is not to be avoided when the first seal is employed together with the balanced seal. In that connection, in summary, the present sealing arrangement is self-balancing and self-regulating; it is automatic and relies on the leakage of the liquid under high pressure in order to maintain and obtain its seal. In comparison, if a balanced seal were used by itself, there would be a considerable dead volume and it would not be possible to isolate the analytical liquid passageway from the sealing mechanism. Also, there is a significant advantage in utilizing a balanced seal which is liquid pressure operated, in that when the pressure is released the device is demountable relatively easily, whereas with seals of other types the sealing forces must be mechanically created so that all of the force necessary to maintain the upper pressure limit would have to be established initially by mechanical force. This would involve a considerable difficulty in connection with assembly of the seal since it must be assembled and taken apart under that pressure. In contrast, the present seal is easily disassembled and is expected to have a lifetime of at least 200 insertions and disassembly steps of a disposable cartridge without requiring replacement of the seal. The latter is easily replaced by use of a dummy plug (not shown), which interfits within the seal and by which the same can be twisted out of position after removal of the retaining ring and then replaced.

By way of further explanation of the character and structure of the flexible plastic member of the ball balance seal, it is preferred to use pure virgin polytetrafluoroethylene, because it is the softest and one of the best sealing materials available at low pressures. Balanced seals are available with reinforcement, however, their ability to seal in the contact with adjacent material is not as high since it does not as easily conform to imperfections on the metal surfaces with which it mates. On the other hand, pure polytetrafluoroethylene is not very strong mechanically. It is for this reason that the retaining ring is employed. While the retaining ring provides a ready solution for two structural features of the coupler of the present invention, other arrangements are possible utilizing, for example, a lip associated with the fitting cupping over a portion of the axially column directed closed end of the balanced seal. This would entail a more difficult replacement, but would be feasible particularly if a reinforced PTFE material were utilized. By way of example, the present invention has employed a ball seal series of 304 as manufactured by Ball Seal Engineering Company of Tustin, Calif., which employs the use of a design utilizing sealing grooves for improved sealing ability. The sealing grooves are arranged to provide labyrinth sealing which serves two functions: (1) a better seal with respect to any roughness in the finish which may exist on the adjacent parts being sealed, and (2) there is some lubrication effect so that movement caused, for example, by differential thermal expansion, does not stress the seal due to the very thin film of liquid wetting the seal.

It is important to realize that while a finger tightenable knurled nut has been shown as the means for delivering through Bellville washer a force carried in tension through a holder, it is possible that for the fitting to be mounted, for example, on a framework and an over center lever utilized to bring a collar or other member pushing against the Bellville washer so as to place the entire assembly into compression. It is not intended that the present invention would be limited by the means for yieldably urging the end fittings together or to be limited to the specific mechanical arrangement of knurled nut and column holder shown. Any means for placing the column in the compression may be utilized, depending upon the application and other practical considerations.

Referring now to FIG. 5, there is shown a union which employs a pair of couplers constructed in accordance with the present invention having common components at the center, so as to form a union capable of joining a guard cartridge to an analytical cartridge directly without any intervening plumbing or piping, tubing or other parts. This has a particular advantage in its capability of providing the function of the guard column while having virtually no degrading effect whatsoever. It also serves as an example of the use of the present invention in a double form to form a union device. Where appropriate like parts in the union of FIG. 4 have been given the same identifying numbers as in FIGS. 1-4 raised by 100. In certain circumstances if identical in construction such parts will be given the same numbers as used in FIGS. 1-4.

More specifically, FIG. 4 shows a union fitting 117 having outwardly threaded exterior contained within a knurled sleeve 109 which is interiorly threaded in a matching manner so that the union fitting can be brought its center. This arrangement is provided as a practical way of constructing the union. Alternatives can easily be envisioned, as for example, the entire sleeve and fitting can be machined out of the same piece, which would, however, have to be chemically inert and thus made of stainless steel. A less costly arrangement is given here where the sleeve is of aluminum cylindrical stock internally threaded while the fitting is stainless steel and externally threaded. Both are easy to manufacture to production tolerances and provide relative displacement to each other to facilitate replacement of seals. As shown, a set screw 121 is employed to fix the relationship between the nut 109 and the fitting 117. The first recess of this fitting is defined laterally by an inwardly extending angular projection of the fitting, having a cylindrical bore 148 therethrough of a dimension similar to that described with respect to the wall 48 of recess of the coupler of FIGS. 1 through 4. This bore is uniform through its length and is sufficiently long to accomodate the axial length of a pair of abutting end plugs and a portion of the tubing of the respective abutting columns, the dimensions being in effect similar to that of FIG. 3. However, the floor of the first recess is defined in this instance by the opposite end plug of the adjacent abutting column.

In other respects, the structure of the balanced seals 111-1 and 111-2 and the annular recesses 160-1, 160-2 in which they are retained is identical to that previously described in connection with recessed 60 and ring 12. Thus, the fitting is formed with oppositely directed circular recesses 160-1, 160-2 constructed in the manner of recess 60 and including outer lateral walls 162-1, 162-2 floors 164-1, 164-2 communicating with the side wall of bore 148. Threaded retaining rings 112-1, 112-2 hold respective balanced seals 111-1, 111-2 in place within the recesses 160-1, 160-2 to form the entire assembly into a unitary structure.

End fittings are provided (not shown) such as those of FIGS. 1-4 for closing the other ends of the guard and analytical columns 113, 114, respectively.

Assembly of this arrangment is exceedingly simple, since the knurled nuts at the opposite ends of the respective assemblies need only be tightened in the manner described with respect to the operation of FIG. 3, the respective Bellville washers operating in the same manner as previously described urge intimate mating contact between the surfaces of the end plugs 34 of the respective columns. Thus, the bore 34a of one end of one column connects directly to the bore of the other column and the first seal is created. Since the seal is of deformable plastic-to-plastic of polytetrafluoroethylene (PTFE), the seal therebetween is even greater than that previously described with respect to stainless steel and PTFE. During operation, leakage of the seal will occur at some high pressure and cause filling of the respective balanced seals to effectuate an operative high pressure seal between the parts exactly in the manner previously described in connection with that of FIGS. 1-3.

Thus, there has been provided an exceptionally effective high-pressure seal for use particularly in liquid chromatography, and an arrangement for providing a guard seal which does not degrade the performance of the system and which serves to increase the useful life of costly analytical columns manyfold. The device is simple to operate in assembly and disassembly. To those skilled in the art which this invention pertains many adaptations and modifications will occur. For example, if it is desired to connect tubing of different sizes, it is obvious that it may be necessary to employ a further element within the union of FIG. 4 to define the floor of the first recess and chamber with a reduction passageway contained therein together with balanced seals of a different size adapted to accomodate the different sizes of tubing. The details of construction and assembly of the device for establishing the compression on the fittings and unions, may be varied while remaining within the scope of the present invention. Accordingly, the present invention should be defined solely by the scope of the following claims interpreted in the light of the foregoing specification.

What is claimed is:

1. Apparatus forming a high pressure coupler for coupling and decoupling a tube to another part to provide a zero dead volume connection therebetween, a fitting connected or associated with said part for high pressure liquid delivery or reception, said fitting including means forming an opening for receiving said tube, said means including a first recess forming a chamber for receiving the end of said tube, means forming a zero dead volume seal between said fitting and said tube, said fitting further including an annular recess spaced away from said chamber in the direction of said tube and surrounding the same, a spring loaded balanced hydraulic seal disposed in said annular recess, means for keeping the balanced liquid pressure actuated seal in said annular recess, said balanced seal being dimensioned to lie in close fitting contact between said tube and the wall defining said annular recess, means within said hydraulic seal for yieldably urging the same between the annular recess and the outer wall of said tube and providing a low pressure seal thereby, said balanced seal being U-shaped in radial cross section and open towards said first seal and chamber so that in operation leakage from the first seal fills the balanced seal to the pressure passing between the tube and coupler to cause radial forces of equal magnitude to be applied between said tube and the wall of said annular recess in said fitting thereby effecting automatic sealing to a pressure equal to the high pressure of the fluid passing therethrough and means for urging the tube and coupler together to establish said first zero dead volume seal.

2. In liquid chromatograph apparatus, a replaceable column cartridge and holder assembly including an LC column, means for closing the ends of said column to form and easily removeable and replaceable unit, said means including deformable portions extending across the end face thereof the full lateral diameter of said column to form a sealing means, a sorbant filling said column, said sealing means having a bore therethrough for admitting liquid under pressure to pass through said sorbant, a fitting for connecting the column to the injection output of a chromatograph means associated with said fitting for connecting the same to the liquid pumping system of a liquid chromatograph and for holding the same in pressure sealed engagement with said fitting, means forming a column receiving recess in the form of an annular wall dimensioned to closer fit about and laterally support said tube and sealing means, means forming a floor across said column receiving recess to define a chamber therewith within which the tube and seal means are positioned so that the sealing means is totally laterally confined within the chamber by its side walls and is axially confined by the column tube and by the floor means to thereby provide said first seal in face to face relation between the column and the floor means of a chamber having zero dead volume therein, a said fitting further including an annular recess surrounding said column and spaced towards the same from said chamber, a liquid pressure operated balanced seal mounted in said recess and having a U-shaped radial cross section opening towards said chamber, means disposed in juxtaposition to the annular recess so as to close the same while permitting the column to be passed therethrough and into said chamber, means for urging the column to effect a sealing relationship having zero dead volume between said column and the means forming the floor of said chamber.

3. Apparatus forming a high pressure union for coupling and decoupling a tubing pair together the latter comprising, a fitting having one end connected to one of said tubing pair, said fitting being open at its other end and formed thereat with the first recess forming at least the lateral wall portion of a chamber for receiving the other tubing end, means forming a zero dead volume seal between the chamber in said fitting and the end of said second tubing, means for urging the tubing pair together to establish said second zero dead volume seal, said end fitting having an annular recess spaced away from said chamber in the direction of said second tube and surrounding the same, a spring loaded balanced liquid pressure actuated seal disposed in said annular recess, means disposed at the second end of said fitting to keep the balanced seal in position in said annular recess, said balanced seal being dimensioned to lie in close fitting contact between the second tube and the wall defining said annular recess within said fitting, means within said balanced seal for yieldably urging the same between said second recess and the outer wall of said tube or column and providing a low pressure seal thereby, said balanced seal including a flexible toroidal shell U-shaped in radial cross section and open towards said first seal and chamber so that, in operation, leakage of the first seal fills the balanced seal to the pressure passing between said tubing pair causing radial forces of equal magnitude to be applied between said second tube and the wall of said annular recess in said fitting thereby effecting automatic sealing to a pressure equal to the high pressure fluid passing through said tubing pair and union.

4. Apparatus forming a high pressure union for coupling and decoupling a tubing pair together the latter comprising, a fitting connected between said tubing pair, said fitting being open at its each end and formed with the a central recess means forming at least the lateral wall portion of a chamber for receiving the respective tubing ends, means for forming at least a portion of means forming a zero dead volume first seal between the recess in said fitting and the ends of said tubing pair, means for urging the tubing pair together to establish said zero dead volume seal, said fitting having annular recesses spaced away from said chamber in the direction of each said tube and surrounding the same, a spring loaded balanced liquid pressure actuated seal disposed in each said annular recess, means disposed at the outer ends of said fitting to keep the respective balanced seal in position in said annular recesses, said balanced seals being dimensioned to lie in close fitting contact between the each of said tubing pair and the wall defining said annular recess within said fitting, means within each said balanced seal for yieldably urging the same between the lateral walls of said annular recesses and the outer wall of the respective tubing and providing a low pressure seal thereby, said balanced seal including a flexible toroidal shell U-shaped in radial cross section and open towards said first seal and chamber so that, in operation, leakage of the first seal fills the balanced seal to the pressure passing between said tubing pair causing radial forces of equal magnitude to be applied between said second tube and the wall of said annular recess in said fitting thereby effecting automatic sealing to a pressure equal to the high pressure fluid passing through said tubing pair and union.

5. Apparatus as in any of claims 1–4 in which said balanced seal includes a flexible toroidal shell made of polytetrafluoroethylene or polytetrafluoropropylene.

6. Apparatus as in claim 2 in which said means for retaining said balanced seal in position includes a retaining ring releasably carried in a sleeve or recess of a surrounding member.

7. Apparatus as in claim 4 in which said tubing pair comprise an analytical LC column and a guard LC column of shorter length than said analytical column.

8. Apparatus as in claim 7 in which the analytical LC column and the guard column are of the same radial dimension in which said recess is formed by a bore of uniform diameter through said fitting so that said columns abut each other in direct end-to-end contact each column serving as the floor of a first zero dead volume chamber and seal for the other.

9. An liquid chromatograph analytical and guard column assembly adapted to be connected to the injection system of the liquid chromatograph to place an analytical column and a guard column in series communication for high pressure operation comprising, a union disposed between said analytical column and said guard column to seal and connect the same together at their one ends in direct end-to-end sealing contact with zero dead volume therebetween, an end fitting disposed at the other ends of each of said guard column and analytical column and including means for establishing a first zero dead volume seal between each said end fitting and the respective volume end, means forming balanced liquid pressure operated secondary seals between the respective ends of the columns and the end fittings and between each side of the union and the other respective abutting ends of the columns, said union and each said end fitting being constructed and arranged so that leakage from said respective first seals of zero dead volume fills the balanced seals to provide operative sealing forces up to the pressure of operation of the system.

10. In a high pressure liquid coupling for placing tubular liquid carrying members in series communication, a union disposed between said members to seal and connect the same together at their one ends in direct end-to-end sealing contact with zero dead volume therebetween, and fitting disposed at the other ends of each of said guard members and including means for establishing a first zero dead volume seal between each said end fitting and respective volume end, means forming balanced liquid pressure operated secondary seals between the respective ends of the columns and the end fittings and between each side of the union and the other respective abutting ends of the columns, said union and each said end fitting being constructed and arranged so that leakage from said respective first seals of zero dead volume fills the balanced seals to provide operative sealing forces up to the pressure of operation of the system.

* * * * *